US00PP35154P2

(12) United States Plant Patent
Berdejo

(10) Patent No.: US PP35,154 P2
(45) Date of Patent: May 2, 2023

(54) ***PULMONARIA* PLANT NAMED 'TNPULRASFRO'**

(50) Latin Name: ***Pulmonaria* spp.**
Varietal Denomination: TNPULRASFRO

(71) Applicant: Terra Nova Nurseries, Inc., Canby, OR (US)

(72) Inventor: Vicenta Herrera Berdejo, Woodburn, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/953,434

(22) Filed: Sep. 27, 2022

(51) Int. Cl.
*A01H 6/00* (2018.01)
*A01H 5/02* (2018.01)

(52) U.S. Cl.
USPC ..... Plt./473

(58) Field of Classification Search
USPC ..... Plt./473
CPC ..... A01H 6/00; A01H 5/02
See application file for complete search history.

*Primary Examiner* — Keith O. Robinson
(74) *Attorney, Agent, or Firm* — The Webb Law Firm

(57) ABSTRACT

A new and distinct *Pulmonaria* plant characterized by leaves having a unique combination of white margins with a frosted, mottled appearance and dark raspberry colored flowers.

2 Drawing Sheets

Botanical classification: *Pulmonaria* spp.
Varietal denomination: 'TNPULRASFRO'.
Commercial trade name: "Raspberry Frost".

BACKGROUND OF THE NEW PLANT

The present invention comprises a new and distinct *Pulmonaria* plant, of the family Boraginaceae, having the varietal name 'TNPULRASFRO'. The new variety originated as a tissue culture mutation of a *Pulmonaria* plant named 'Raspberry Splash' (U.S. Plant Pat. No. 12,138). The new variety was discovered as a spontaneous mutation in a batch of tissue culture plants in Canby, Oreg.

When compared to its parent, *Pulmonaria* plant named 'Raspberry Splash', the new variety has a smaller, more compact habit and exhibits cream variegation in an irregular fashion on the leaves. When compared to *Pulmonaria rubra* plant named 'David Ward' (unpatented), the new variety has narrower leaves of a gray-green color rather than yellow-green, more mottling on the leaves, and coral rather than dark raspberry colored flowers.

The new variety has only been reproduced by asexual propagation (division and tissue culture). Each of the progeny exhibits identical characteristics to the original plant. Asexual propagation by division and tissue culture performed in Canby, Oreg. shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Pulmonaria* plants known to the breeder, the new variety is characterized by the following:

1. Irregularly margined, white-edged variegation on lanceolate leaves;
2. Gray-green mottled leaves with silvery overlay covering 90 percent of the leaf area; and
3. High vigor.

DESCRIPTION OF THE DRAWINGS

The accompanying photographic drawings illustrate the new variety at approximately 1 year of age, with the colors being as nearly true as possible with color illustrations of this type.

DETAILED BOTANICAL DESCRIPTION

Figure 1:
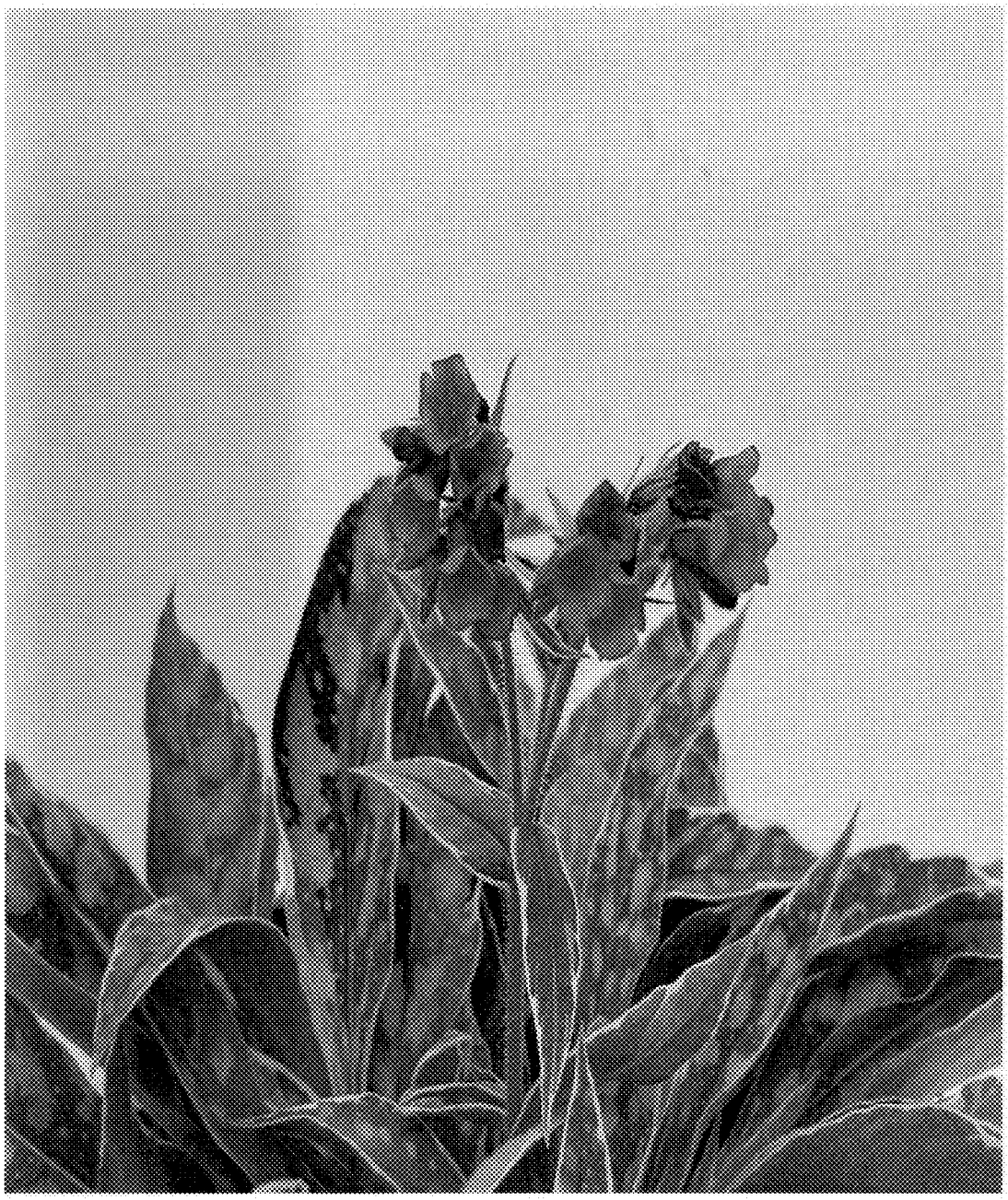
FIG. 1 illustrates a close-up of view of the leaves and flowers of the new variety in Canby, Oreg. in April.
Figure 2:
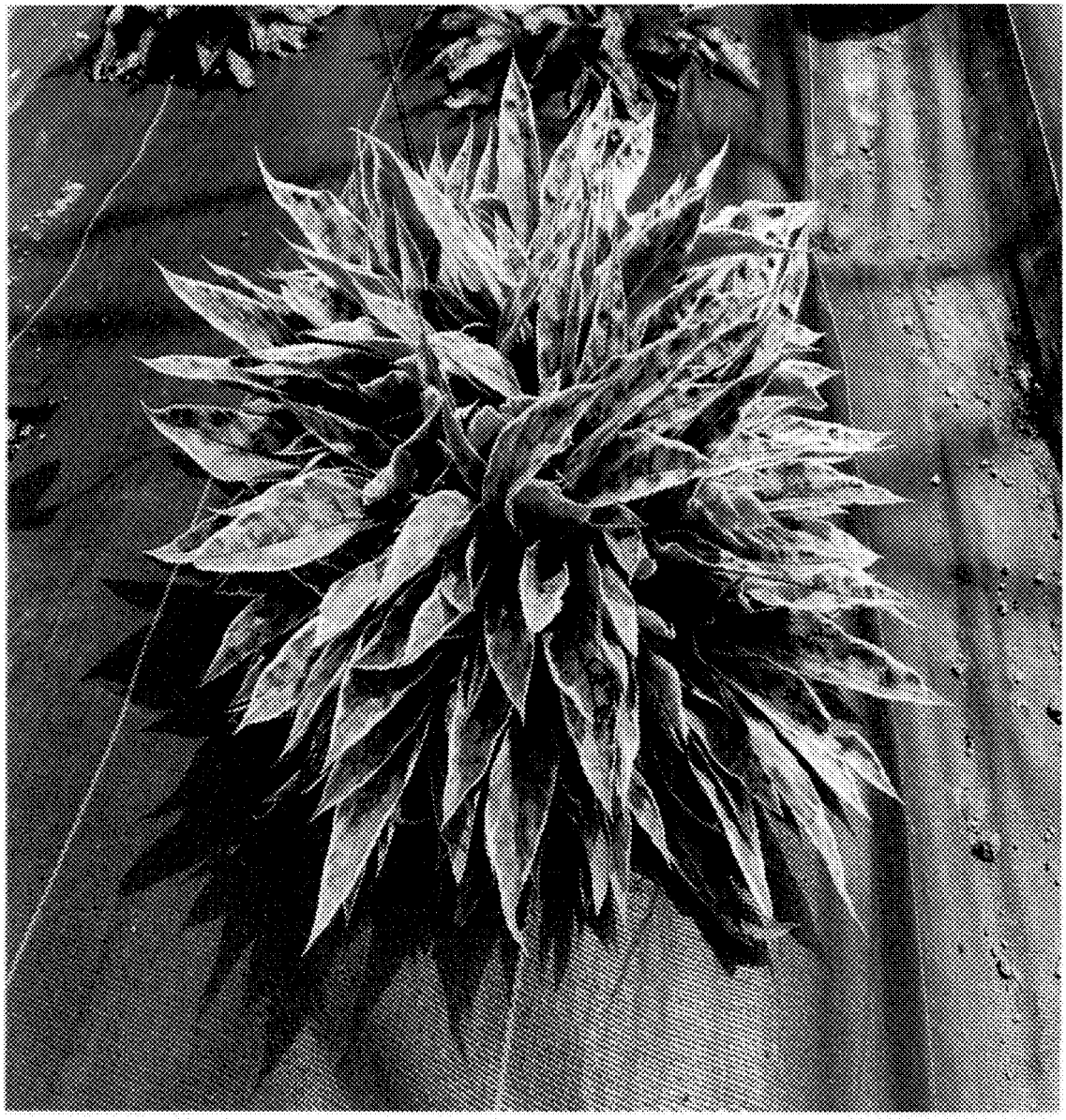
FIG. 2 illustrates an original plant in a trial field in Canby, Oreg. in June.

The following is a detailed description of the new variety based on observations of 1½ year old plants grown under field conditions in Canby, Oreg. Color references are based on The 2007 R.H.S. Colour Chart of The Royal Horticultural Society of London, 5$^{th}$ Edition.

Plant:

*Type*.—Herbaceous perennial.
*Hardiness*.—USDA Zones 4 to 9.
*Size*.—35.0 cm wide and 20.0 cm tall.
*Form*.—Basal clump.
*Vigor*.—High.
*Root description*.—Fine, fibrous, and plentiful. The youngest roots are RHS N155A and the oldest roots near the crown are RHS 156D.

Foliage:

*Type*.—Simple.
*Leaf arrangement*.—Rosette.
*Shape*.—Lanceolate.
*Length*.—15.0 to 28.0 cm.
*Width*.—2.75 to 3.75 cm.
*Margin*.—Entire, ciliate, irregularly undulating.
*Apex*.—Narrowly acute.
*Base*.—Attenuate.

*Leaf texture* (*both surfaces*).—Setose; irregularly rugose.

*Upper surface color*.—RHS 191A, with occasional patches or streaks of N189B. The mottled area is RHS 190C and the margins are RHS 155B.

*Lower surface color*.—RHS 191B.

*Venation*.—Reticulate-pinnate.

*Petiole length*.—12.0 to 15.0 cm.

*Petiole texture*.—Setose.

*Petiole color*.—RHS 191B.

Flowers:

*Bud*.—Length: 12.0 mm. Width: 3.0 mm. Shape: Ovoid. Color: RHS 60C.

*Type*.—Complete; perfect.

*Inflorescence type*.—Forked cymes, numbering from 9 to 17 per plant.

*Flower number per inflorescence*.—12 to 28.

*Bloom period*.—Middle of March to early June in Canby, Oreg.

*Fragrance*.—None.

*Lastingness* (*inflorescence*).—7-10 days on the plant if not pollinated; 2-4 days off the plant or if pollinated.

*Shape*.—Campanulate.

*Size*.—7.0 to 9.0 mm from petal tip to petal tip.

*Corolla*.—Arrangement: 5 fused petals with rounded lobes. Depth: 2.0 cm. Width: 1.5 cm. Tube size: 9.0 mm long and 3.0 mm deep. Lobes: Depth: 3.0 mm. Width: 5.0 mm. Margins: Entire. Tips: Obtuse. Texture: Satiny. Color: Inside color of RHS 51A, the outside color is RHS 51B on the cup, RHS 60B on the top half of the tube, and RHS NN155D on the bottom half.

*Calyx*.—Arrangement: 5 fused sepals. Size: 1.5 cm deep and 1.0 cm wide. Texture: Setose. Color: RHS 160A.

*Sepals*.—Number: 5. Length: 12.0 mm. Width: 2.5 mm across the base, 7.0 mm at fused base. Apex: Narrowly acute. Texture: Hispid. Color: RHS 147B.

*Peduncle*.—Height: 15.0 to 20.0 cm. Width: 3.0 mm, tapering to 1.5 mm at apex. Texture: Setose. Color: RHS N144C.

*Pedicel*.—Length: 2.0 to 10.0 mm. Texture: Hispid. Color: RHS 200B.

*Ovary*.—Partly inferior position; 1.2 mm in diameter; RHS 146D in color.

*Carpel number*.—4.

*Pistil*.—1; pin type, exerted from the corolla tube and about 13.0 mm long.

*Style*.—Cylindrical; glabrous; 7.0 mm long and 0.5 mm wide.

*Stigma*.—Slightly rounded apex; 0.5 mm in diameter and 0.04 mm high; RHS 157A.

*Stamen*.—5 anthers in number; RHS 203B; 2.0 mm in length.

*Anthers*.—Attached to and inserted in the top of the corolla tube; 2.2 mm long and 1.0 mm in diameter; RHS N186B.

*Filament*.—3.0 mm long; RHS 155C.

*Pollen*.—Scarce; RHS NN155A.

Seeds:

*Type*.—4 smooth nutlets.

*Size*.—0.4 cm long.

*Shape*.—Ovoid.

*Color*.—RHS 200A.

*Fertility*.—Unknown.

Pests/diseases: No unusual resistance or susceptibility noted to date.

I claim:

1. A new and distinct variety of *Pulmonaria* plant named 'TNPULRASFRO', substantially as illustrated and described herein.

* * * * *